US008080550B2

(12) United States Patent
Horn

(10) Patent No.: US 8,080,550 B2
(45) Date of Patent: Dec. 20, 2011

(54) ANESTHETIC COMPOSITIONS AND METHODS OF USE

(75) Inventor: Gerald Horn, Deerfield, IL (US)

(73) Assignee: Alpha Synergy Development, Inc., Dana Point, CA (US)

( * ) Notice: Subject to any disclaimer, the term of this patent is extended or adjusted under 35 U.S.C. 154(b) by 138 days.

(21) Appl. No.: 12/460,954

(22) Filed: Jul. 27, 2009

(65) Prior Publication Data

US 2010/0029661 A1 Feb. 4, 2010

Related U.S. Application Data

(60) Provisional application No. 61/137,714, filed on Aug. 1, 2008, provisional application No. 61/192,777, filed on Sep. 22, 2008, provisional application No. 61/203,120, filed on Dec. 18, 2008, provisional application No. 61/207,481, filed on Feb. 12, 2009.

(51) Int. Cl.
*A61K 31/495* (2006.01)
*A61K 31/41* (2006.01)
(52) U.S. Cl. ........................ 514/249; 514/359
(58) Field of Classification Search .................. 514/249, 514/359
See application file for complete search history.

(56) References Cited

U.S. PATENT DOCUMENTS

| | | | |
|---|---|---|---|
| 4,663,340 | A | 5/1987 | Najer et al. |
| 5,021,416 | A | 6/1991 | Gluchowski |
| 5,300,504 | A | 4/1994 | Gluchowski |
| 5,424,078 | A | 6/1995 | Dziabo et al. |
| 5,561,132 | A | 10/1996 | Burke et al. |
| 5,677,321 | A | 10/1997 | Jeon et al. |
| 5,756,503 | A | 5/1998 | Burke et al. |
| 5,804,587 | A | 9/1998 | Cupps et al. |
| 5,914,342 | A | 6/1999 | Maurer et al. |
| 5,916,900 | A | 6/1999 | Cupps et al. |
| 5,948,804 | A | 9/1999 | Jeon et al. |
| 5,965,595 | A | 10/1999 | Maurer et al. |
| 6,040,451 | A | 3/2000 | Jeon et al. |
| 6,087,361 | A | 7/2000 | Munk et al. |
| 6,110,952 | A | 8/2000 | Henry et al. |
| 6,117,871 | A | 9/2000 | Maurer et al. |
| 6,159,998 | A | 12/2000 | Jeon et al. |
| 6,162,818 | A | 12/2000 | Henry et al. |
| 6,242,442 | B1 | 6/2001 | Dean et al. |
| 6,534,048 | B1 | 3/2003 | Borgman |
| 6,562,873 | B2 | 5/2003 | Olejnik et al. |
| 6,627,210 | B2 | 9/2003 | Olejnik et al. |
| 6,641,834 | B2 | 11/2003 | Olejnik et al. |
| 6,673,337 | B2 | 1/2004 | Olejnik et al. |
| 6,730,065 | B1 | 5/2004 | Horn |
| 6,982,079 | B2 | 1/2006 | Huth |
| 2005/0020600 | A1 | 1/2005 | Scherer |

OTHER PUBLICATIONS

Medical Management of Chronic Rhinosinusitus— Jean P. Fong, MD, Matthew Ryan, MD (May 2006).
Preven Drugs from Going Missing in Action—Mark B. Abelson, MD, and Sarah A. Rosner MPH; Review of Ophthalmology; www.revophth.com/index.asp?page=1_357.htm.
Interactions Between CA2+ and H+ and Functional Consequences in Vascular Smooth Muscle—C. Austin and S. Wray, Journ. of Amer. Heart Association (Circ Res. 2000;86:355-363).
A Useful New Topical Treatment For Glaucoma And Ocular Hypertension—Drug Ther Perspect 13(1):1-4, 1999.
Brimonidine In The Treatment of Glaucoma and Ocular Hypertension—Louis B. Cantor, Therapeutics And Clinical Risk Management 2006:2(4) 337-346.
Silent Bedpartners—Nancy A. Collop, Chest 2002; 122; 1111-1112.
Traitement Des Glaucomes Par La Brimonidine (Alphagan® 0,2 %)—M. Detry-Morel, C. Dutrieux, J Fr. Ophtalmol., 2000; 23, 8, 763-768.
Vasopressin-Induced Vasoconstriction: Two Concentration-Dependent Signaling Pathways—Kyle K. Henderson and Kenneth L. Bryon, J Appl Physiol 102: 1402-1409, 2007.
The Effect Of Correction Of Sleep-Disordered Breathing On Bp In Untreated Hypertension—K. MAE HLA, J. B. Skatrud, L. Finn, M. Palta and T. Young, Chest 2002;122; 1125-1135.
Myogenic Tone And Reactivity Of The Rat Ophthalmic Artery—Y. P. R. Jarajapu, M. B. Grant, and H. J. Knot, Invest. Ophth. & Visual Science, Jan. 2004, vol. 45, No. 1.
Correspondence A Propos De L'article: <<Traitement Des Claucomes Par La Brimonidine>>, M. Detry-Morel ET C. Dutrieux, J Fr Ophtalmol. 2000; 23(8): 763-8.
Prospective Study Of The Association Between Sleep-Disordered Breathing and Hypertension—P. Peppard, et. al., The New England J of Med., vol. 342, No. 19:1378-1384 (2000).
Catecholamines And Sympathomimetic Drugs—Goodman & Gilman's Pharmacology, Ch. 10; www.accessmedicine.com/popup.aspx?aID-936314&pring=yes_chapter.
Rhinitis Medicamentosa—JT Ramey, E Bailen, RF Lockey, J Investig Allergol Clin Immunol 2006; vol. 16(3); 148-155.
Characterization of three inhibitors of endothelial nitric oxide synthase in vitro and in vivo—D.D. Rees, et al., br. J. Pharmacol. (1990) 101, 746-752.
Inhibition of α-adrenergic vasoconstriction in exercising human thigh muscles—D. Walter Wray, et al., J Physiol 555, 2 pp. 545-264 (2003).
Dexmedetomidine Enhances the Local Anesthetic Action of Lidocaine via . . . Tatsushi Yoshitomi DDS et al., Anesth Analg 2008; 107:96-101.
Adding Dexmedetomidine to Lidocaine for Intravenous Regional Anesthesia, Dilek Memis, MD et al., Anesth Analg 2004;98:835-40.
Mechanism of decongestant activity of x2-adrenoceptor agnosits, Corboz M.R. et al., Pulmonary Pharmacology & Therapeutics 21 (2008) 449-454.
Alpha-adrenoceptor agonistic activity of oxymetazoline and xylometazoline, Haenisch B. et al., Fundam Clin Pharmacol. Dec. 17, 2009.

(Continued)

*Primary Examiner* — Sreeni Padmanabhan
*Assistant Examiner* — Renee Claytor
(74) *Attorney, Agent, or Firm* — Wood, Philips, Katz, Clark & Mortimer

(57) ABSTRACT

The invention generally relates to anesthetic compositions comprising low doses of a selective a-2 adrenergic receptor agonists in combination with anesthetic agents. The invention also relates to methods of using these compositions; in particular, the use of these compositions in humans to enhance the efficacy of a local peripheral anesthetic injection. The compositions and the methods are particularly useful in regional block anesthetic injections, and more particularly, in dental anesthetic injections.

9 Claims, 1 Drawing Sheet
(1 of 1 Drawing Sheet(s) Filed in Color)

OTHER PUBLICATIONS

An Evaluation of Nasal Response Following Different Treatment Regimes of . . . , Morris S. et al., American Journal Rhinology, vol. 11, No. 2, Mar.-Apr. 1997, pp. 109-115(7).

Pharmacological Characterization of Postjunctional a-Adrenoceptors in . . . , Corboz M.R. et al., American Jour of Rhinology, vol. 19, No. 5, Sep.-Oct. 2005, pp. 495-502(8).

Postjuntional a2-adrenoceptors in blood ve3ssels of human nasal mucosa, Ichimura K. et al., Arch Otorhinolaryngol (1988) 245:127-131.

Long-term use of oxy- and xylometazoline nasal sprays induces rebound swelling, tolerance, and nasal hyperreactivity, Graf P., Rhinology 1996, 34(1):9-13.

Alpha 1-receptors at pre-capillary resistance vessels of the human nasal mucosa, Johannssen V et al., Rhinology 1997; 35(4):161-65.

Correspondence A Propos De L'article: <<Traitement Des Glaucomes Par La Brimonidine>>, M. Detry-Morel ET C. Dutrieux< J Fr Ophtalmo1.2001; 24(7): 748-9.

Potent a2A-Adrenoceptor-Mediated Vacoconstriction by Brimonidine in Porcine Ciliary Arteries, Anna Wikberg-Matsson, et al., IOVS, 2001, vol. 42, No. 9, 2049-55.

Medical Management of Chronic Rhinosinusitus—Jean P. Fong, MD, Matthew Ryan, MD (May 2006).

ANESTHETIC COMPOSITIONS AND METHODS OF USE

BACKGROUND OF THE INVENTION

It is known that combining a vasoconstrictor with an anesthetic during anesthetic injection reduces the risk of anesthetic toxicity resulting from systemic absorption. In particular, lidocaine may be associated with rare malignant hyperthermia and/or cardiovascular collapse and arrest. Use of a vasoconstrictor together with an anesthetic reduces systemic absorption to the anesthetic and increases the anesthetic's local tissue retention time before its eventual dilution via diffusion. It also allows the anesthetic to metabolize more slowly, until local vasoconstriction is reversed.

Currently, epinephrine is most commonly used in combination with lidocaine in concentrations ranging from 0.0000001% to about 0.0001% weight by volume. However, because epinephrine is one of the most powerful alpha 1 agonists, significant cardiovascular side effects may occur, with an increased risk of hypertension, stroke, arrhythmia or infarction, particularly, in individuals with a history of cardiovascular disease. This risk increases exponentially in cases where an inadvertent intraarteriolar injection may occur, which may happen especially when the anesthetic injection is used for regional nerve block.

Accordingly, there is a need to optimize vasoconstriction during anesthesia without systemic negative side effects caused by epinephrine.

SUMMARY OF THE PRESENT INVENTION

In one embodiment, the invention generally relates to an anesthetic composition comprising an anesthetic agent and a selective a-2 adrenergic receptor agonist having a binding affinity of 500 fold or greater for a-2 over a-1 adrenergic receptors, or a pharmaceutically acceptable salt thereof, wherein said selective a-2 adrenergic receptor agonist is present at a concentration below about 0.05% weight by volume, and wherein the total volume of the anesthetic composition to be administered to a patient is from about 1 ml to about 50 ml, and wherein the concentration of said selective a-2 adrenergic receptor agonist is between 1:300,000 to 1:2,500,000.

Preferably, the concentration of said selective a-2 adrenergic receptor agonist is between $1 \times 10^{-4}$ M and $5 \times 10^{-6}$ M, and even more preferably, between $3 \times 10^{-4}$ M and $2.5 \times 10^{-6}$ M.

In a more preferred embodiment, the selective a-2 adrenergic receptor agonist is a compound which has binding affinity of about 700 fold or greater for a-2 over a-1 adrenergic receptors In a preferred embodiment, the selective a-2 adrenergic receptor is dexmeditomidine.

In a more preferred embodiment, the anesthetic compositions of the invention are to be used in a regional block anesthesia. In a more preferred embodiment, the anesthetic compositions of the invention are to be used in dental anesthetic injections.

In a preferred embodiment, the ratio of a selective a-2 adrenergic receptor agonist to an anesthetic is between 1:300,000 to 1:2,500,000.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

Figure 1:
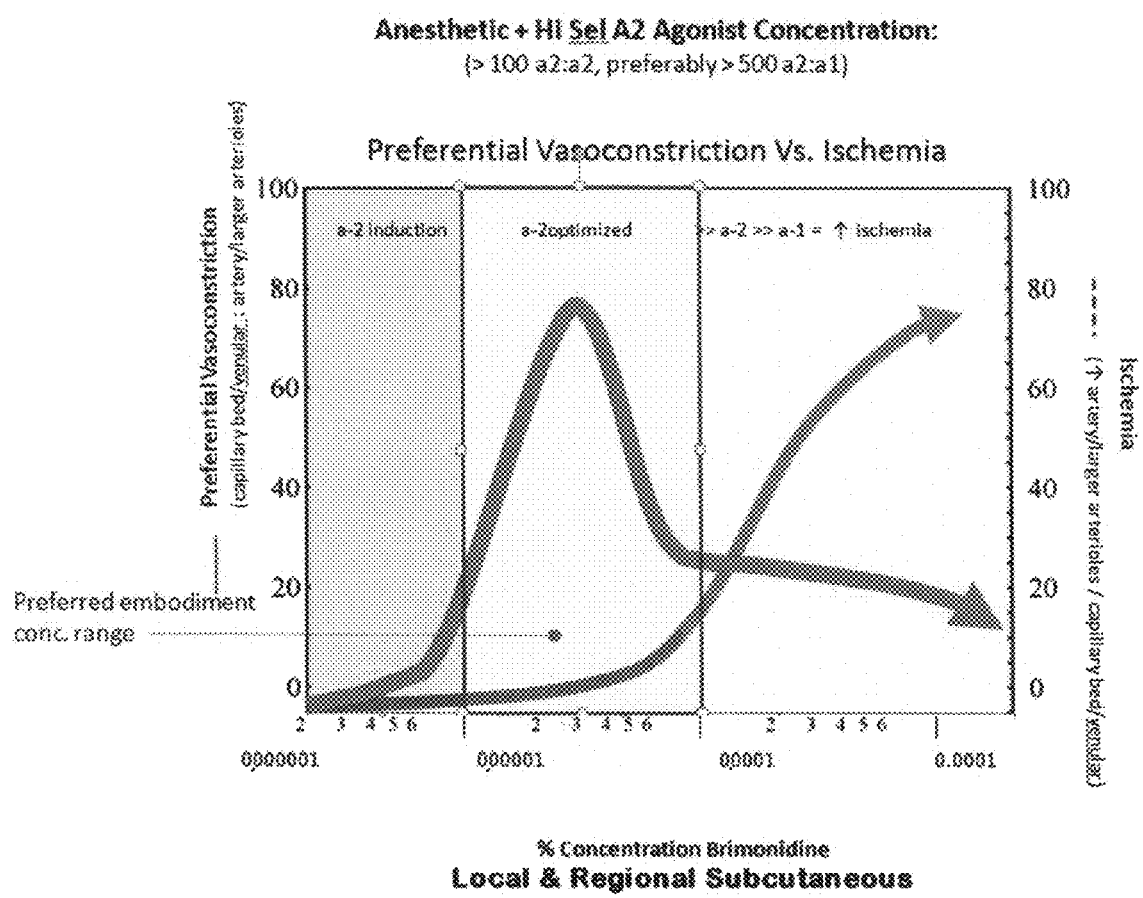
FIG. 1 is a graphical representation of preferential vasoconstriction and ischemia at various concentrations of brimonidine.

For purposes of the present invention, the terms below are defined as follows.

The term low concentration refers to a concentration relative to that normally used for anesthetic injection into tissue (dermis, or intramuscular injection, most typically, and/or regional block anesthesia, particularly for dental application), where 1:100,000 to 1:200,000 ratios of epinephrine to anesthetic are typically used.

The term "administered locally" refers to administering the compositions of the present invention approximately at the site where they will come into contact with a-2 adrenergic receptors. This term specifically excludes oral administration, intravenous injection, or transdermal patches which are not applied approximately at the spatial location of the area which is desired to be treated by the compositions of the present invention.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan™, and UK14304.

The term "patient" refers to a human being.

Anesthetic Applications

It is one discovery of the present invention that the use of selective alpha 2 agonists, preferably having a binding affinity of 500 fold or greater for a-2 over a-1 adrenergic receptors, provides sufficient a-1 and a-2 receptor activity to optimize the effectiveness of the vasoconstriction from both receptors and to reduce anesthetic risk and risk of cardiovascular events triggered by a-1 and/or -1 receptor stimulation.

To maximize anesthetic retention in local tissue space and minimize both anesthetic and vasoconstrictor systemic toxicity, a selective a-2 adrenergic receptor agonist that is used in combination with a topical anesthetic agent may have some a-1 agonist activity, yet the degree of a-1 receptor stimulation must be sufficiently low to minimize the known cardiovascular risks associated with alpha 1 agonists at high concentrations and to minimize vasoconstriction of larger and more proximal high oxygen saturated arteries and arterioles vs. more distal vessels in the large artery to smaller artery, arterioles, capillary bed, benules and large vein cycle of oxygen transport to and from tissue.

It is the belief of the inventor that a combination of an anesthetic for tissue injection and the selective a-2 receptor agonist results in preferential vasoconstriction of microvessels and venules versus arteries and larger arterioles. This combination could provide reduced ischemia with maximal microvascular and/or venular constriction resulting in equal or greater retention of anesthetic circumscribing the region injected, reduced ischemia, possibly reduced systemic absorption (preferentially, microvessels and venules), less risk of systemic toxicity, and quicker recovery once anesthetic wears off due to reduced ischemia, all with reduced systemic risk.

It is the inventor's belief that significant β receptor and a-1 receptor agonist induced vasoconstriction resulting from epinephrine use increases ischemia, prolongs recovery relative to the adaptation of the present invention for this purpose, and increases well documented a-1 related systemic risks. As there are hundreds of millions of anesthetic blocks given per year, cases of arterial injection further add morbidity form systemic absorption, in particular, in dental applications, where even a low incidence of complications represents a significant quantified morbidity.

For the purposes of the present invention, it is then desirous to obtain preferential terminal arteriole and/or effective microvessel (capillary) and venular constriction over larger arterial or non-terminal arteriolar vasoconstriction to minimize diffusion of anesthetic injected into tissue, reduce systemic absorption, and maximize potential enhancement of anesthetic effect with least morbidity.

Thus, in one embodiment, the invention relates to optimizing a-2 agonist receptor activation while minimizing a-1 receptor activation.

The methods and compositions of the present invention require both a highly selective a-2 agonist, with much higher binding affinities for a-2 over a-1 adrenergic receptors (at least 100 fold or greater for a-2 over a-1; preferably, 500 fold or greater; and even more preferably, 700 fold or greater), and proper dose response selection of low concentrations to avoid sufficient a-1 receptor trigger and/or excessive a-2 dosing that could increase undesirable effects.

The following Table 1 illustrates the preferred compositions of intradermal injection of selective alpha agonist.

| Concentration Lidocaine HCl | Brimonidine/ Dexmeditomidine | Lidocaine HCl (anhyd.) mg/mL | Sodium Chloride mg/mL |
|---|---|---|---|
| 0.5% | 1:300,000 to 1:2,500,000 | 5 | 8 |
| 1% | 1:300,000 to 1:2,5,000,000 | 10 | 7 |
| 1.5% | 1:300,000 to 1:2,5,000,000 | 15 | 6.5 |
| 2% | 1:300,000 to 1:2,5,000,000 | 20 | 6 |
| 1% | 1:400,000 to 1:5,000,000 | 10 | 7 |
| 2% | 1:400,000 to 1:5,000,000 | 20 | 6 |
| 0.5% | 1:30,000 to 1:250,000 | 5 | 8 |
| 1% | 1:30,000 to 1:250,000 | 10 | 7 |
| 1.5% | 1:30,000 to 1:250,000 | 15 | 6.5 |
| 2% | 1:30,000 to 1:250,000 | 20 | 6 |
| 1% | 1:40,000 to 1:500,000 | 10 | 7 |
| 2% | 1:40,000 to 1:500,000 | 20 | 6 |

Preferred embodiments of the present invention include brimonidine and/or dexmeditomidine instead of epinephrine in the concentration ranges indicated above. The use of lower doses compared to epinephrine further reduces systemic risk, alpha 1 agonist induced ischemia and systemic risk, and optimizes preferential microvascular vs. larger vessel constriction.

In preferred embodiments, the formulations of the present invention will further include sodium metabisulfite 0.5 mg/mL and citric acid, anhydrous 0.2 mg/mL added as stabilizers. The compositions may also contain sodium hydroxide and/or hydrochloric acid to adjust pH; pH is typically in a range of 4.5 to 5.5, and is most preferably about 5.0.

In one embodiment, the invention generally relates to an anesthetic composition comprising an anesthetic agent and a selective a-2 adrenergic receptor agonist having a binding affinity of 500 fold or greater for a-2 over a-1 adrenergic receptors, or a pharmaceutically acceptable salt thereof, wherein said selective a-2 adrenergic receptor agonist is present at a concentration below about 0.05% weight by volume, and wherein the total volume of the anesthetic composition to be administered to a patient is from about 1 ml to about 50 ml, and wherein the concentration of said selective a-2 adrenergic receptor agonist is between 1:300,000 to 1:2,500,000.

Preferably, the concentration of said selective a-2 adrenergic receptor agonist is between $1 \times 10^{-4}$ M and $5 \times 10^{-6}$ M, and even more preferably, between $3 \times 10^{-4}$ M and $2.5 \times 10^{-6}$ M.

In a more preferred embodiment, the selective a-2 adrenergic receptor agonist is a compound which has binding affinity of about 700 fold or greater for a-2 over a-1 adrenergic receptors Preferably, the total volume of the anesthetic composition is from about 1 ml to about 25 ml; more preferably, from about 1 ml to about 20 ml; and even more preferably, from about 2 ml to about 18 ml. The volume is dependent on the patient's weight.

In a preferred embodiment, the selective a-2 adrenergic receptor for use in the method of enhancing the efficacy of a local peripheral anesthetic injection is dexmeditomidine or brimonidine. In a more preferred embodiment, said selective a-2 adrenergic receptor agonist concentration is from about 0.0000001% to about 0.0001% weight by volume.

In a more preferred embodiment, the anesthetic compositions of the invention are to be used in a regional block anesthesia. In a more preferred embodiment, the anesthetic compositions of the invention are to be used in dental anesthetic injections.

In a preferred embodiment, the ratio of a selective a-2 adrenergic receptor agonist to an anesthetic agent is between 1:300,000 to 1:2,500,000.

In another preferred embodiment, the anesthetic agent is selected from the group consisting of xylocaine, lidocaine, and mixtures thereof.

In one preferred embodiment, the invention generally relates to an anesthetic composition comprising lidocaine and dexmedetomidine, wherein said dexmedetomidine concentration is between about 0.0000001% and about 0.0001% weight by volume, more preferably 0.000001% to 0.000030% and even more preferably 0.00001% to 0.00020% weight by volume, and wherein the total volume of the anesthetic composition to be administered to a patient is from about 1 ml to about 50 ml.

In another preferred embodiment, the invention generally relates to a method of enhancing the efficacy of a local peripheral anesthetic injection, comprising administering locally to a patient in need thereof the anesthetic composition according to the present invention.

Preferably, the methods of enhancing the efficacy of a local peripheral anesthetic rejection also cause preferential vasoconstriction of smaller blood vessels (such as capillaries and venules) relative to larger blood vessels (such as arteries and arterioles).

Also, preferably, the methods of enhancing the efficacy of a local peripheral anesthetic rejection simultaneously reduce ischemia and enhance retention and/or action of the local anesthetic agent.

In another preferred embodiment, the compositions useful for these purposes comprise an anesthetic agent and brimonidine at concentrations of from about 0.0000001% to about 0.0001% weight by volume.

Selective a-2 Adrenergic Receptor Agonists

Selective a-2 agonists that may be used for the purposes of the present invention have extremely high selectivity for a-2 adrenergic receptors, defined by their binding affinities ($K_i$) for a-2 over a-1 receptors of more than 100:1, more preferably 500:1, even more preferably 700:1, even more preferably 1000:1 or greater, and most preferably, 1500:1 or greater.

It is well within a skill in the art to design an assay to determine a-2/a-1 functional selectivity. As non-limiting examples, potency, activity or $EC_{50}$ at an a-2A receptor can be determined by assaying for inhibition of adenylate cyclase activity. Furthermore, inhibition of adenylate cyclase activity can be assayed, without limitation, in PC12 cells stably expressing an a-2A receptor such as a human a-2A receptor. As further non-limiting examples, potency, activity or $EC_{50}$ at an a-1A receptor can be determined by assaying for intracellular calcium. Intracellular calcium can be assayed, without limitation, in HEK293 cells stably expressing an a-1A receptor, such as a bovine a-1A receptor.

To the best of the inventor's knowledge, and not desiring to be bound by any specific theory or mechanism, it is believed by the inventor that the particularly preferred adrenergic receptor agonists for the purposes of the present invention are highly selective for a-2B and/or a-2C receptors, as opposed to a-2A receptors.

Generally, there is an inverse relationship between the selectivity and the agonist concentration: the more selectivity (i.e., the higher binding affinity for a-2 adrenergic receptors), the lower concentrations may be effective for purposes of the present invention.

In one embodiment, the selective a-2 adrenergic receptor agonist is a compound which has binding affinity of about 100 fold or greater for a-2 over a-1 adrenergic receptors. When a2/a1 is less than about 500 fold but more than about 100 fold, a concentration of the selective a-2 agonist is preferably from about 0.01% to about 0.07%; and is more preferably from about 0.02% to about 0.04%.

In a preferred embodiment, the selective a-2 adrenergic receptor agonist is a compound which has binding affinity of about 500 fold or greater for a-2 over a-1 adrenergic receptors. When a2/a1 is less than about 800 fold but more than about 500 fold, a concentration of the selective a-2 agonist is preferably from about 0.005% to about 0.05%; and is more preferably from about 0.01% to about 0.02%.

In a more preferred embodiment, the selective a-2 adrenergic receptor agonist is a compound which has binding affinity of about 700 fold or greater for a-2 over a-1 adrenergic receptors. When a2/a1 is less than about 1200 fold but more than about 800 fold, a concentration of the selective a-2 agonist is preferably from about 0.001% to about 0.025%; and is more preferably from about 0.005% to about 0.01%.

In a more preferred embodiment, the selective a-2 adrenergic receptor agonist is a compound which has binding affinity of about 1000 fold or greater for a-2 over a-1 adrenergic receptors. When a2/a1 is less than about 2000 fold but more than about 1200 fold, a concentration of the selective a-2 agonist is preferably from about 0.0005% to about 0.01%; and is more preferably from about 0.0025% to about 0.005%.

In a more preferred embodiment, the selective a-2 adrenergic receptor agonist is a compound which has binding affinity of about 1500 fold or greater for a-2 over a-1 adrenergic receptors. When a2/a1 is more than about 2000 fold, a concentration of the selective a-2 agonist is preferably from about 0.0002% to about 0.005%; and is more preferably from about 0.001% to about 0.003%.

The selective a-2 adrenergic receptor agonist may be present at a concentration from between about 0.0001% to about 0.05%; more preferably, from about 0.001% to about 0.025%; even more preferably, from about 0.01% to about 0.025%; and even more preferably, from about 0.01% to about 0.02% weight by volume.

It is preferred that a concentration of a selective a-2 adrenergic receptor agonist be below its vasoconstriction vs. concentration plateau. Typically, the optimal concentration is 10% to 90% above the minimal threshold of measurable vasoconstriction for a particular a-2 agonist, or below that of the plateau maximum concentration, and is preferably within the about 25% to about 75% range of either of these benchmarks. The term "plateau maximum concentration" means the concentration above which there is no or minimal further vasoconstriction effect. Other considerations in choosing a selective a-2 adrenergic receptor agonist are blood brain permeability and any possible side effects and other systemic reactions.

In one embodiment, the selective a-2 adrenergic receptor is selected from the group consisting of apraclonidine, mivazerol, clonidine, brimonidine, alpha methyl dopa, guanfacine, dexemeditomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds. Analogs of these compounds that function as highly selective a-2 agonists may also be used in compositions and methods of the present invention.

Compositions (Formulations)

Anesthetic compositions of the present invention may be prepared by skilled artisans without undue experimentation. Generally, a simple solution is made, wherein an anesthetic is combined with a selective a-2 agonist.

They anesthetic compositions may also include additional non-therapeutic components, which include, but are not limited to, preservatives, delivery vehicles, tonicity adjustors, buffers, pH adjustors, antioxidants, and water.

The preservatives include, but are not limited to, benzalkonium chloride, chlorobutanol, thimerosal, phenylmercuric acetate, or phenylmercuric nitrate. Vehicles useful in a topical ophthalmic composition include, but are not limited to, polyvinyl alcohol, povidone, hydroxypropyl methyl cellulose, poloxamers, carboxymethyl cellulose, hydroxyethyl cellulose and purified water.

A tonicity adjustor also can be included, if desired, in an anesthetic composition of the invention. Such a tonicity adjustor can be, without limitation, a salt such as sodium chloride, potassium chloride, mannitol or glycerin, or another pharmaceutically or ophthalmically acceptable tonicity adjustor.

Various buffers and means for adjusting pH can be used to prepare an anesthetic composition in the invention. Such buffers include, but are not limited to, acetate buffers, citrate buffers, phosphate buffers and borate buffers. It is understood that acids or bases can be used to adjust the pH of the composition as needed. The acceptable antioxidants useful in preparing a topical composition include, but are not limited to, sodium metabisulfite, sodium thiosulfate, acetylcysteine, butylated hydroxyanisole and butylated hydroxytoluene.

The present invention is more fully demonstrated by reference to the accompanying drawings.

FIG. 1 depicts a graphical representation of preferential vasoconstriction and ischemia at various concentrations of the highly selective a-2 agonist (e.g., brimonidine). Generally, at low concentrations of highly selective a-2 agonists, there is 1) preferential vasoconstriction of microvessels and/or venules versus larger arteries and arterioles, and 2) low a-1 receptor agonist activity. This results in per unit area show high degree of tissue vasoconstriction with minimal ischemia. The tissue vasoconstriction reduces absorption, and possibly, metabolism of an anesthetic, and increases retention within the tissue area being infiltrated.

As the concentration of the a-2 agonist increases, the total pool of triggered a-1 receptors also increases. The excessive a-2 and a-1 receptor stimulation (i.e., the stimulation above that needed for the ED 100 for microvessels and/or venules)

has no known beneficial effects and causes increased ischemia with attendant inflammatory change.

The invention claimed is:

1. An anesthetic composition comprising an anesthetic agent, wherein said anesthetic agent is selected from the group consisting of xylocalne, lidocaine, and mixtures thereof, and brimonidine or a pharmaceutically acceptable salt thereof, wherein brimonidine is present at a concentration below about 0.05% weight by volume, wherein the total volume of the anesthetic composition to be administered to a patient is from about 1 ml to about 50 ml, and wherein the concentration of brimonidine is between $1\times10^{-4}$ M and $5\times10^{-6}$ M.

2. The anesthetic composition of claim 1 wherein the concentration of brimonidine is between $3\times10^{-4}$ M and $2.5\times10^{-6}$ M.

3. The anesthetic composition of claim 1, wherein brimonidine is present at a concentration from between about 0.0001% to about 0.00005% weight by volume.

4. The anesthetic composition of claim 1, wherein the ratio of brimonidine to said anesthetic agent is between 1:30,000 to 1:250,000.

5. An anesthetic composition comprising an anesthetic agent, wherein said anesthetic agent is selected from the group consisting of xylocalne, lidocaine, and mixtures thereof, for a dental injection and brimonidine, wherein said brimonidine concentration is from between about 0.0000001% to about 0.0001% weight by volume, wherein the total volume of the anesthetic composition is from about 1 ml to about 50 ml, and wherein the ratio of said brimonidine to said anesthetic agent is between 1:30,000 to 1:250,000.

6. A method of enhancing the efficacy of a local peripheral anesthetic injection, comprising administering locally to a patient in need thereof the anesthetic composition according to claim 1.

7. A method of enhancing the efficacy of a local peripheral anesthetic injection, comprising administering locally to a patient in need thereof the anesthetic composition according to claim 1, wherein said method induces preferential vasoconstriction of smaller blood vessels relative to larger blood vessels.

8. An anesthetic composition comprising an anesthetic agent, wherein said anesthetic agent is selected from the group consisting of xylocalne, lidocaine, and mixtures thereof, and brimonidine, or a pharmaceutically acceptable salt thereof, wherein said ratio of anesthetic to selective a-2 adrenergic receptor agonist is 1:30,000 to 1:250,000 wherein the total volume of the anesthetic composition to be administered to a patient is from about 1 ml to about 50 ml.

9. The method of claim 6, wherein said method further results in a simultaneous reduction of ischemia and enhanced retention of said anesthetic agent.

* * * * *

UNITED STATES PATENT AND TRADEMARK OFFICE
CERTIFICATE OF CORRECTION

PATENT NO.       : 8,080,550 B2
APPLICATION NO.  : 12/460954
DATED            : December 20, 2011
INVENTOR(S)      : Gerald Horn It is certified that error appears in the above-identified patent and that said Letters Patent is hereby corrected as shown below:

Claim 1, column 7, line 6 word xylocalne - should be "xylocaine"

Claim 5, column 7, line 25 word xylocalne - should be "xylocaine"

Claim 8, column 8, line 17 word xylocalne - should be "xylocaine"

Signed and Sealed this
Twenty-second Day of May, 2012

David J. Kappos
*Director of the United States Patent and Trademark Office*